(12) United States Patent
Falvo D'urso Labate (10) Patent No.: US 12,084,647 B2
(45) Date of Patent: Sep. 10, 2024

(54) DEVICE FOR A CELL SUSPENSION CULTURE

(71) Applicant: CELLEX S.R.L., Rome (IT)

(72) Inventor: Giuseppe Falvo D'urso Labate, Rome (IT)

(73) Assignee: CELLEX S.R.L., Rome (IT)

( * ) Notice: Subject to any disclaimer, the term of this patent is extended or adjusted under 35 U.S.C. 154(b) by 434 days.

(21) Appl. No.: 17/269,649

(22) PCT Filed: Oct. 28, 2019

(86) PCT No.: PCT/IB2019/059212
§ 371 (c)(1),
(2) Date: Feb. 19, 2021

(87) PCT Pub. No.: WO2020/095143
PCT Pub. Date: May 14, 2020

(65) Prior Publication Data
US 2021/0340484 A1    Nov. 4, 2021

(30) Foreign Application Priority Data

Nov. 9, 2018   (IT) ................ 102018000010212

(51) Int. Cl.
*C12M 1/42*     (2006.01)
*C12M 1/00*     (2006.01)
*C12M 1/34*     (2006.01)

(52) U.S. Cl.
CPC .......... *C12M 35/04* (2013.01); *C12M 23/02* (2013.01); *C12M 41/32* (2013.01)

(58) Field of Classification Search
CPC ....... C12M 35/04; C12M 23/02; C12M 41/32; C12M 27/18
See application file for complete search history.

(56) References Cited

U.S. PATENT DOCUMENTS 6,082,705 A * 7/2000 Arvidsson ........... A61M 16/206
251/129.17
9,475,686 B2 * 10/2016 Tuohey .................. C12M 29/14
(Continued)

FOREIGN PATENT DOCUMENTS

WO         2012157007 A1    11/2012

OTHER PUBLICATIONS

International Search Report and Written Opinion dated Jan. 3, 2020; 40 pages.

*Primary Examiner* — William H. Beisner
*Assistant Examiner* — Danielle B Henkel
(74) *Attorney, Agent, or Firm* — Mark Malek; Widerman Malek, PL (57) ABSTRACT

The device for a cell suspension culture comprises a culture chamber comprising first and second axisymmetric-shaped walls having at least a partially curved radial section the concavity thereof facing the inside of the culture chamber, the walls delimiting an inner compartment and form an inner continuous surface; an inlet opening provided in the first wall and adapted to enable a fluid to enter; a supplying conduit connected to the inlet opening; and a valve member disposed inside the culture chamber adapted to tightly close or open the inlet opening. The device comprises also a device for moving the valve member, disposed outside the culture chamber.

13 Claims, 4 Drawing Sheets

(56) References Cited

U.S. PATENT DOCUMENTS

| | | | | |
|---|---|---|---|---|
| 2007/0148726 A1* | 6/2007 | Auton | ................... | C12M 23/02 |
| | | | | 366/151.1 |
| 2016/0186124 A1* | 6/2016 | Jäger | ..................... | C12M 41/00 |
| | | | | 435/289.1 |
| 2017/0191016 A1* | 7/2017 | Lee | ....................... | C12M 23/14 |

* cited by examiner

DEVICE FOR A CELL SUSPENSION CULTURE

Related Applications

This application is a national phase application of and claims priority under 35 U.S.C. § 371 of PCT Application Serial No. PCT/IB2019/059212 filed on Oct. 28, 2019 and titled DEVICE FOR A CELL SUSPENSION CULTURE, which claims the benefit of IT 102018000010212, filed on Nov. 9, 2018, each of which is hereby incorporated by reference in its entirety.

TECHNICAL FIELD OF THE INVENTION

The present invention refers to a cell suspension culture device.

PRIOR ART

Cell culture devices, known also as microgravity generating devices, where cells suspended in a fluid moving inside a flow chamber or culture chamber are cultured, are known.

The size of such devices can range from few milliliters to several tens of liters and are used in laboratories for performing tests on cells cultured in a suspension, or in an industrial field for mass producing cells for scientific or industrial uses, or in a vaccines manufacturing chain.

In the known devices, the suspension is obtained both in an active way or passive way.

In the "active" devices, the suspension is obtained by rotating components driven by dedicated actuators. However, such devices have the disadvantage of requiring sophisticated couplings for driving the rotating components outside the flow chamber, consequently securing the tightness and sterilization of the inside of the flow chamber is problematic.

Moreover, manufacturing these devices is expensive due to the high cost of the components, and they have a high operating cost due to the great amount of power required for performing a culture.

On the contrary, in the "passive" devices, interfaces in which the thrust on the entering fluid causes valves to open, which in turn close when the fluid pressure is interrupted, are provided. The disadvantages consist of the complexity of said interface, and implementing the same interface is unstable, which in turn makes unstable the motion field inside the flow chamber. Such instability makes impossible to ensure the repeatability of the results in a laboratory and makes ineffective the use of these "passive" devices in the industrial field.

Moreover, the requirement of activating the actuation system by thrusting it through the pressurized entering fluid strongly jeopardies the scalability because, as the size increases, the weight increase of the valve requires inlet pressures greater than the ones which are considered economically sustainable.

These "passive" devices have a further limit because they require the presence of a containment filter for preventing the culturing cells from leaking. This filter is jammed not only by the cells themselves, but also by proteins produced by the latter which, by coming in contact with the filter and denaturing themselves, jam the pores and consequently restrict the disposal of the catabolites produced by the cells themselves (which causes a risk of poisoning the culture environment) and also prevent a correct duration of the culture before completely jamming the filter.

It is also noted that all these devices, both "active" and "passive", do not ensure a correct diffusion of oxygen and nutrients in the area of the motion field in which the cells are suspended. This implies a low growth and production rates, which can be only empirically evaluated.

Documents EP2265708, RU2355751, US2011/0027880, WO2008073348 and US2010/0120136 illustrate some examples of cell suspension culture devices as hereinbefore described.

Patent application WO2012157007 illustrates a passive type cell suspension culture device, provided with a flow chamber having sloped lateral walls, optimized for generating a microgravity inside it. However, such device does not solve the problem of the stability in the motion field because the valve is opened only by the entering fluid thrust. Further, this device neither overcomes the problem of the presence of the filter, nor enables to obtain a good distribution of oxygen inside the flow chamber.

BRIEF SUMMARY OF THE INVENTION

Therefore, the object of the present invention is the implementation of a cell suspension culture device which enables to generate a microgravity without rotating members, in a controlled way at a low cost.

In the scope of such task, it is a further object of the invention making a cell suspension culture device producing a microgravity in which the motion field is stable.

Another object of the invention consists of making a cell suspension culture device ensuring a good oxygen and nutrients concentration in the cell culture zone.

Still another object of the invention consists of making a cell suspension culture device where containment filters are not required.

This and other objects are met by a cell suspension culture device according to claim 1.

The dependent claims define possible advantageous embodiments of the invention.

BRIEF DESCRIPTION OF THE DRAWINGS

In order to better comprehend the invention and appreciate the advantages thereof, some exemplifying non-limiting embodiments will be described in the following with reference to the attached drawings, wherein.

DESCRIPTION OF THE EMBODIMENTS OF THE INVENTION

A cell suspension culture device, according to the invention, is indicated by reference 1 in the attached figures. The cell culture device 1 is of a passive type because it does not comprise any rotating components for generating the microgravity.

Figure 1A:
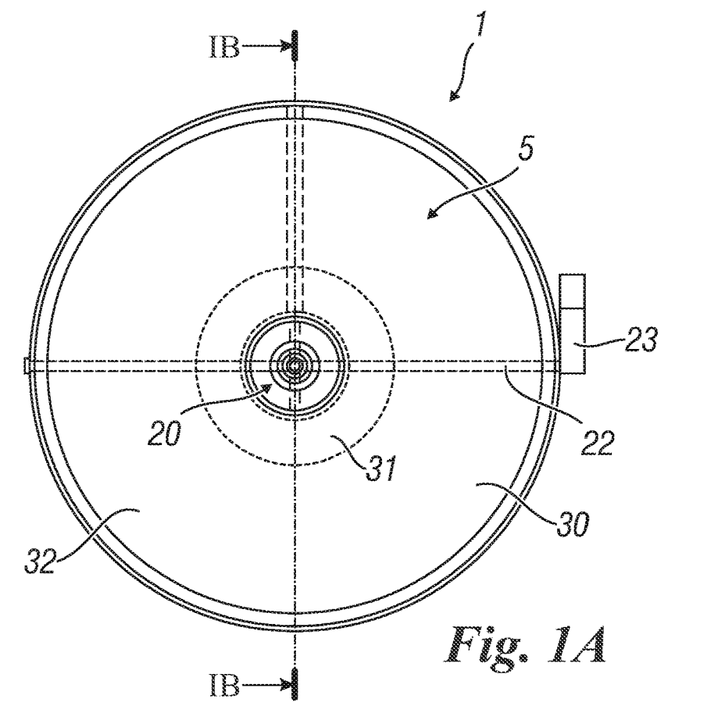
FIG. 1A illustrates a plan view of the cell suspension culture device according to a first embodiment of the invention, in a first operative configuration.
Figure 1B:
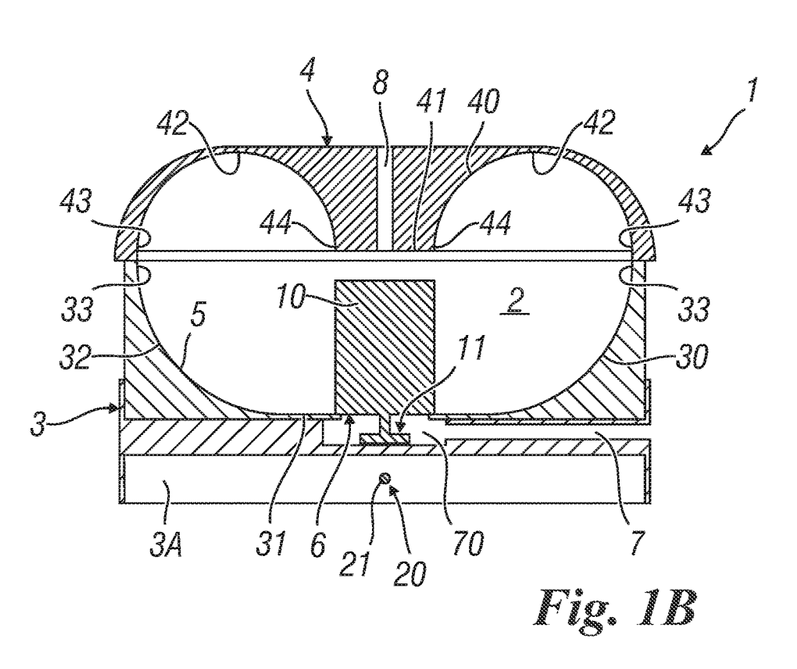
FIG. 1B is a lateral cross-section view taken along the axis IB-IB of FIG. 1A.

Generally, the cell suspension culture device 1 comprises a culture chamber 2 comprising a first wall 30 and a second wall 40 defining an inner compartment. The first 30 and second walls 40 have an axisymmetric shape with an at least partially curved radial cross-section having the concavity facing the inside of the culture chamber 2, and they are connected to each other in order to form a continuous inner surface 5 (FIGS. 1A and 1B).

The term "inner surface 5" means, in the scope of the present invention, a surface substantially devoid of discontinuities (particularly at the joint between the outer edges of the first wall 30 and second wall 40) except obviously for possible inlet or outlet openings, particularly interruptions and sharp-edge angles or corners. Possible angles or corners of the inner surface 5 are chamfered.

The example of FIGS. 1A, 1B, 2A and 2B shows the first wall 30 located below the second wall 40. In other words, the first wall 30 is the lower wall of the culture chamber 2, while the second wall 40 is the upper wall. It is possible to provide the opposite.

As the Figures show, preferably the device 1 comprises a base body 3 and a lid 4 adapted to be tightly connected to the base body 3, specifically at the perimetral edge. One of the first 30 and second walls 40 is disposed in the base body 3, while the other ivvvs disposed in the lid 4. In the illustrated examples, the first (lower) wall 30 is disposed in the base body 3 and the second (upper) wall 40 is disposed in the lid 4.

It is observed that the base body 3 defines the culture chamber 2 in the upper portion thereof, in other words the wall 30, 40 of the culture chamber 2 is disposed in the upper portion, facing the upper end of the base body 3. Moreover, it is particularly advantageous to provide a lower compartment 3A comprised in the base body 3 and disposed below the wall 30, 40 of the culture chamber 2.

Preferably, the lid 4 can be made of a transparent material, for monitoring the culture during its development.

Moreover, the device 1 comprises an inlet opening 6 provided in the first wall 30 and adapted to enable a fluid to enter the culture chamber 2. Such fluid supplied inside the culture chamber 2 is the way by which the microgravity required for the cell suspension culture, is generated.

Further, the device 1 comprises, for this purpose, a supply conduit 7 connected to the inlet opening 6 and adapted to enable the fluid to be supplied to the culture chamber 2 through the inlet opening 6. It is observed that the supply conduit 7 is obviously connected to a fluid source and also to a pressurized fluid supplying means, for example a pump. Consequently, the fluid is supplied under pressure and in a controlled way towards the inside of the culture chamber 2. Obviously, the supply conduit 7 is completely outside the culture chamber 2.

Figure 2A:
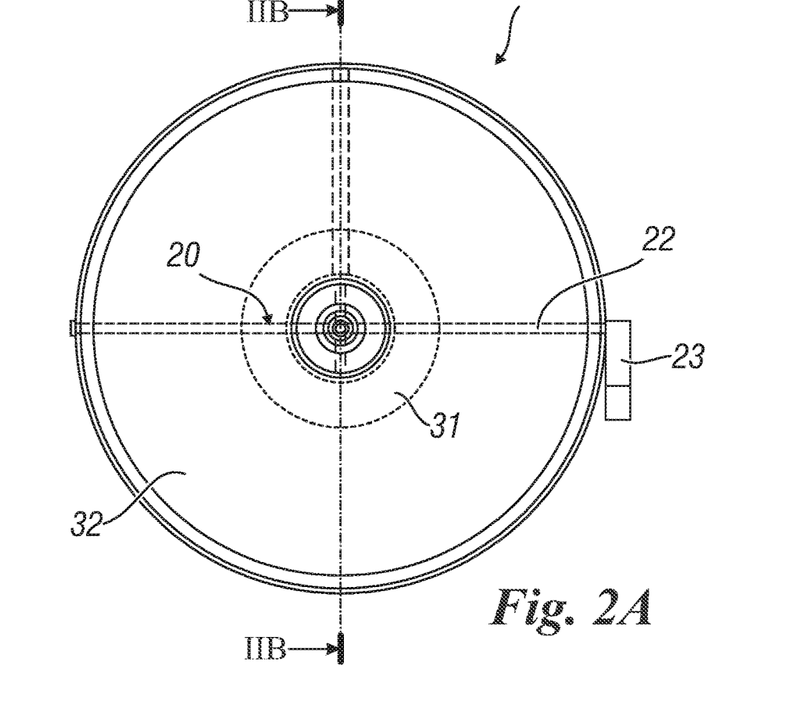
FIG. 2A is a plan view of the device of FIG. 1, in a second operative configuration.
Figure 2B:
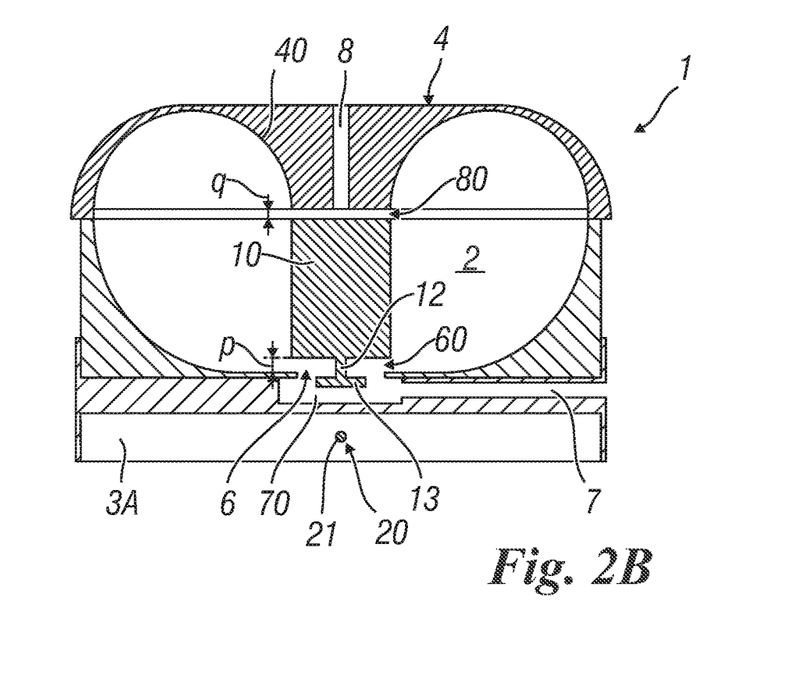
FIG. 2B is a lateral cross-section view taken along the axis IIB-IIB of FIG. 2A.

As it is shown in FIGS. 1B and 2B, the supply conduit 7 is connected to the inlet opening 6 preferably through a pre-chamber 70 made outside the culture chamber 2 but communicating with the latter by the inlet opening 6.

Preferably, the supply conduit 7 and pre-chamber 70 are arranged in the base body 3 of the device 1. More preferably, the supply conduit 7 and pre-chamber 70 are located between the culture chamber 2 and the lower compartment 3A of the base body 3.

In order to interrupt the fluid supply, the device 1 comprises also a valve member 10 placed inside the culture chamber 2 at the inlet opening 6 and movable between a closed position wherein the valve member 10 tightly closes the inlet opening 6 (FIGS. 1A and 1B), and an open position, wherein the valve member 10 is distanced from the inlet opening 6 and enables the outflow of the fluid to the inside of the culture chamber (FIGS. 2A and 2B).

Advantageously, the valve member 10 comprises an interaction portion 11 disposed at least partially outside the culture chamber (FIGS. 1B, 2B, 3 and 4). The interaction portion 11 comprises for example a rod 12 extending from the valve member 10 and provided at the free end thereof with an interaction member 13, which in the illustrated example, is in the shape of a disc. In the illustrated examples, the interaction portion 11 is suitably placed inside the pre-chamber 70.

Preferably, the device 1 comprises retaining means adapted to retain at least partially the interaction portion 11 of the valve member 10 outside the culture chamber 2. Such retaining means can be for example provided at the inlet opening and are adapted to lock the interaction portion 11 (e.g. the disc 13) without jamming the inlet opening 6.

According to a further advantageous aspect of the invention, the valve member 10 is in a cylindrical shape and is arranged parallel to the symmetry axis of the culture chamber 2. Still more preferably, the valve member 10 is arranged coaxially with the culture chamber 2. The two terminal surfaces of the valve member are preferably flat, particularly the one which is destined to tightly close the inlet opening 6.

According to the present invention, the cell suspension culture device 1 comprises a device 20 for moving the valve member 10, adapted to cause this latter to move between the open position and the closed position. Such movement device 20 is arranged outside the culture chamber 2. Otherwise, none of the components of the movement device 20 enters the culture chamber 2, not even partially.

The presence of the movement device 20, for moving the valve member 10 enables to generate a microgravity without the presence of rotating members, in a controlled way and at a low cost. A further advantage of the device 1, according to the invention, consists of creating the microgravity in a stable motion field, which enables to obtain microgravity conditions which can be repeated due to the presence of the device 20 for moving the valve member 10. The valve member 10, by the device 20, is not only moved by the entering fluid, so that the latter can therefore preserve its flow rate when arrives inside the culture chamber 2.

According to an advantageous variation of the invention, the first wall 30 comprises a lower zone 31 and a joint zone 32 adapted to connect to each other the lower zone 31 and second wall 40 (FIGS. 1B and 2B). The joint zone 32 has an arc-of-circle cross-section having a concavity facing the inside of the culture chamber 2.

The lower zone 31 is disposed centrally with respect to the first wall 30 and is surrounded by the joint zone 32 (FIGS. 1A and 2S). Preferably, both these zones have an axisymmetric shape, particularly an annular one. Preferably, the lower zone has a flat surface. It is also preferred to place the inlet opening 6 in the lower zone 31, as shown in the figures.

Again advantageously, the arc-of-circle of the cross-section of the joint zone forms an angle substantially equal to 90°, so that the inner surface 5 is substantially vertical at the perimetral edge of the first wall 30. Consequently, the continuity between the first 30 and second walls 40 is promoted when both are reciprocally connected.

Particularly, it is also advantageous to provide that the second wall 40 comprises a central zone 41 and an annular zone 42 surrounding the central zone 41 (FIGS. 1B and 2B). The annular zone 42 has an arc-of-circle cross-section the concavity thereof facing the inside of the culture chamber 2. It has a perimetral edge 43 adapted to be connected to the perimetral edge 33 of the first wall 30, and preferably an inner edge 44 delimiting the annular zone 42 of the central zone 41.

Preferably, the inner surface 5 of the culture chamber 2 is substantially vertical at the perimetral edge 43 of the second wall 40, in order to be connected to the perimetral edge 33 of the first wall 30 without any discontinuities. Still more preferably, the cross-section of the annular zone 42 forms an angle substantially equal to 180° (the cross-section of the annular zone 42 is a semicircle) so that the inner surface 5 is substantially normal both to the perimetral edge 43 and the inner edge 44.

The central zone 41 is advantageously provided with a flat surface.

According to another particularly advantageous aspect of the invention, the central zone 41 of the second surface 40 has a diameter substantially equal to the diameter of the cylindrical valve member 10. Consequently, the inner surface 5 of the culture chamber 2 is joined or substantially joined also to the outer surface of the valve member 10, which advantageously promotes a better fluid circulation, and therefore a more efficient microgravity inside the culture chamber 2.

According to a preferred aspect of the invention, when the valve member 10 is in the open position, it opens a port 60 for a fluid flow, the height thereof p being predetermined with respect to the first wall 30. "Height p of the port 60" means, in the scope of the present invention, the minimum distance between the lower zone 31 and the valve member 10 taken parallelly to the symmetry axis of the culture chamber 2, if the surfaces of the lower zone 31 and valve member 10 are not parallel to each other and/or are not perfectly flat.

"Predetermined height p" means that the displacement of the valve member 10 to the open position determines a height p of a port 60 which is always the same from one displacement to another (is repeatable) but also during the same displacement. Such predetermined height p can be obtained, for example, by the rod 12 which extends from the valve member 10 and by the presence of suitable retaining means at the inlet opening 6, adapted to retain the disc 13 so that it does not exit the pre-chamber 70. In this case, the rod 12 has a length equal to the desired height p.

It was discovered that such height p of the port 60 can be a useful parameter on which the geometry of the culture chamber 2 can be calculated in order to optimize the microgravity inside the chamber.

Indeed, it was demonstrated that it is particularly advantageous and preferable if the cross-section of the joint zone 32 of the first wall 30 had a curve radius comprised between five and twenty times the height p of the port 60. More preferably, the curve radius of the cross-section of the joint zone 32 is comprised between seven and thirteen times the height p of the port 60. Optimally, the curve radius of the cross-section of the joint zone is ten times the height p of the port 60.

Similarly, it was demonstrated that is particularly advantageous if the curve radius of the cross-section of the annular zone 42 of the second surface 40 was comprised between three and ten times the height p of the port 60, and less than the curve radius of the cross-section of the joint zone 32 of the first surface 30. More preferably, the curve radius of the annular zone 42 is comprised between five and eight times the height p of the port 60. Still more preferably, the curve radius of the annular zone 42 is equal to 6.5 times the height p of the port 60.

These features enable to obtain a good distribution and diffusion of the oxygen and nutrients inside the culture chamber 2. It was observed that with the hereinbefore cited parameters, the obtained results are the optimal ones. However, it is outlined that acceptable results, particularly in terms of stability of the motion field, are obtained with curve radiuses which are outside the identified intervals.

According to a preferred variant of the invention, the cell suspension culture device 1 comprises also an outlet opening 8 enabling the fluid to exit the culture chamber 2. The outlet opening 8 is disposed in the second wall 40 (FIGS. 1B, 2B, 3 and 4).

Preferably, the outlet opening 8 is placed in the central zone 41 of the second wall 40, still more preferably, is disposed coaxially with the culture chamber 2. Consequently, the outlet opening 8 is in the shape of a conduit connecting the inside of the culture chamber 2 to the outside. It is observed that it is advantageously provided the outlet opening 8 with a diameter less than or equal to the height p of the port 60.

It is also observed that in order to enable the fluid to correctly exit any time, the member is distanced from the surface of the central zone 41 of the second wall 40 also when is in the open position, so that is does not close the outlet opening 8. Still more advantageously, the valve member 10, when is in the open position, forms an outlet port 80 having a predetermined height q and substantially equal to the height p of the port 60.

According to a first embodiment of the invention (FIGS. 1A, 1B, 2A, and 2B), the movement device 20 of the valve member 10 comprises a magnetic element 21, the valve member 10 being provided with a magnetic counter-element adapted to interact with the magnetic element 21.

Advantageously, the magnetic counter-element is disposed in the interaction portion 11 of the valve member, in order to improve the interaction with the magnetic element 21. Still more preferably, the magnetic counter-element comprises a disc 13.

It is also advantageous to provide the movement device 20 in the base body 3, and more particularly in the lower compartment 3A of the base body 3, in order to optimize the interaction with the interaction portion 11 of the valve member 10.

Possibly, provision can also be made for the magnetic-type movement device 20 to be manually actuatable. For example, as it can be seen in FIGS. 1A and 2A, the movement device 20 comprises a rod 22 substantially radially placed with respect to the culture chamber 2 (anyway in a position so that a portion thereof is placed at the valve member 10) and provided with a lever 23 disposed outside the base body. The magnetic element 21 can be fixed to the rod 22 or is integrated with it, in order to be moved between a first position determining the displacement of the valve member to the closed position (FIGS. 1A and 1B, the opposite poles respectively of the magnetic element 21 and magnetic counter-element face each other), and a second position determining the displacement of the valve member 10 to the open position of the inlet opening 6 (FIGS. 2A and 2B, the corresponding poles respectively of the magnetic element 21 and magnetic counter-element face each other).

It is observed that the illustrated example provides a manual actuation of the movement device 20, however it is possible to provide also an actuation by an electric actuator.

It is also observed that the presence of a magnetic-type movement device 20 is particularly adapted to small-sized devices, typically having an overall volume less than 500 ml of the culture chamber, for example destined to a laboratory use.

The motion field and oxygen concentration were analyzed by a computer simulation in order to evaluate the efficiency of the device 1 about the microgravity conditions and correct distribution of oxygen inside the culture chamber 2.

In the used model, the cell suspension culture device 1 is of a type illustrated in the figures. Specifically, the inlet opening 6, valve member 10 and outlet opening 8 are coaxial with each other and with the culture chamber 2. The diameter of the central zone 41 of the second wall 40 is equal to the diameter of the valve member 10 which is cylindrical. The curve radius of the cross-section (forming a fourth circle) of the joint zone 32, is equal to 10 p and the curve radius of the cross-section of the annular zone 42 (forming a semicircle) is equal to 6.5 p. The diameter of the outlet opening 8 is equal to the height p of the port 60. The first wall 30 is the lower wall of the chamber 2, while the second wall 40 is the upper wall.

Figure 3:
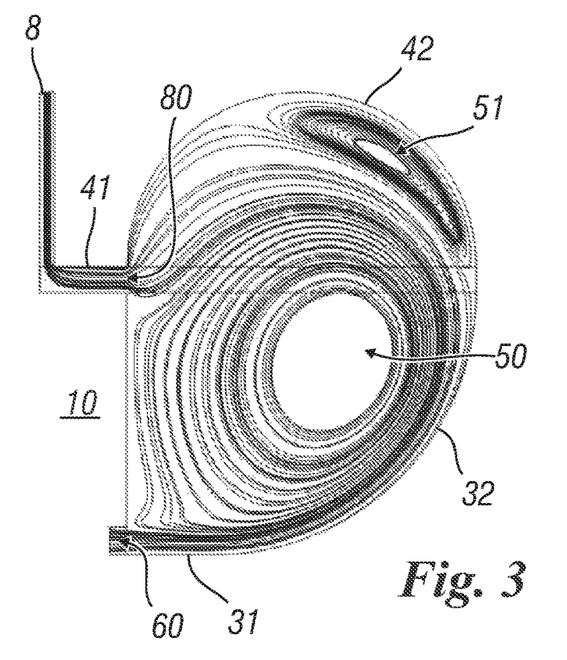
FIG. 3 is an axisymmetric map discretized in the motion field of a fluid supplied inside the cell suspension culture device according to the invention during the culture.

FIG. 3 shows a representation of the motion field. It illustrates how a vortex is formed at the joint zone 32 of the first wall 30, which forms a confinement zone 50 of the culture cells. The cell suspension culture is provided in this confinement zone 50.

Such confinement zone is obtained by the curve and concave shape of the first wall 30, in other words the lower one. The radius of such curvature cooperates to determine the size of the confinement zone 50.

It is also noted that a second vortex is formed in the annular zone 42 of the second wall 40. Such second vortex forms a zone 51 collecting the cells possibly escaped from the motion field, and also proteins and catabolites produced by them. Consequently, the catabolites are confined outside the confinement zone 50, and therefore they do not pollute the culture environment.

Figure 4:
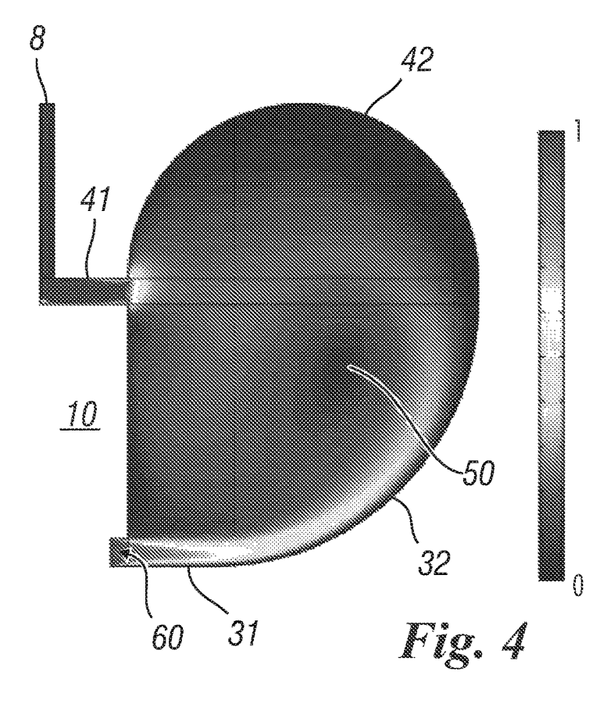
FIG. 4 is a colorimetric map normalized to one of the oxygen concentration inside the cell suspension culture device, in comparison with the inlet oxygen concentration during the culture.

On the contrary, FIG. 4 illustrates the oxygen concentration in the culture chamber 2. The simulation shows that a greater oxygen concentration is obtained just in the confinement zone 50, wherein the cell suspension culture is maintained, and gradually decreases outside the confinement zone 50, until the oxygen is almost absent along the inner surface 5 of the culture chamber 2. This low oxygen concentration outside the confinement zone 50 proves that the losses are at a minimum.

It is also noted that the oxygen concentration in the confinement zone 50, normalized to 1 with respect to the supplying oxygen concentration, in other words the one present in the fluid supplied to the inside of the culture chamber 2 and from the outside, is substantially equal to the one of the fluid entering the device.

These results are excellent and are obtained by curve radiuses optimized as a function of the parameter p. As hereinbefore discussed, acceptable results are obtained by curve radiuses not comprised in the hereinbefore cited intervals, for example the motion field comprises only the confinement zone 50, and/o the same confinement zone 50 has a size different from the size given as an example.

Figure 5:
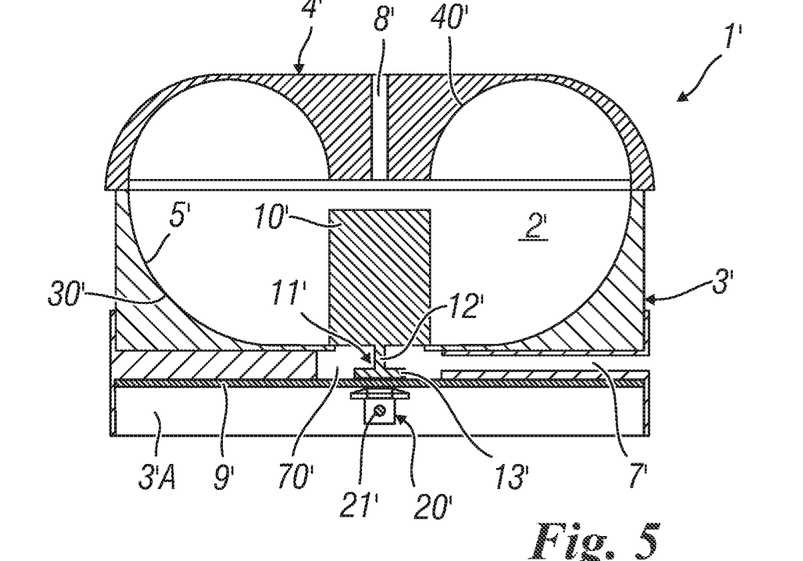
FIGS. 5 and 6 illustrate a lateral cross-section view of the cell suspension culture device according to a second embodiment, respectively in a first and second operative configuration.
Figure 6:
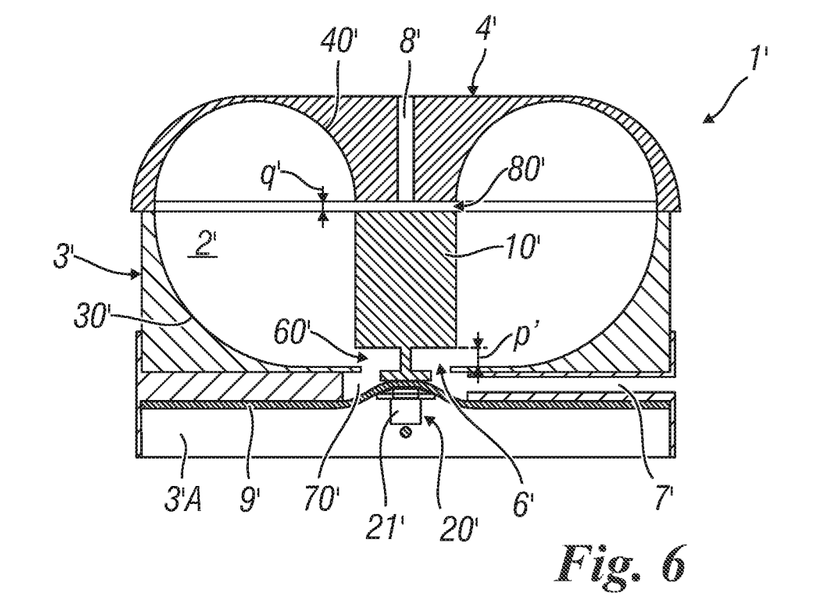

With reference to FIGS. 5 and 6, they illustrate a second embodiment of the cell suspension culture device. The elements common to the first embodiment will not be described again, for the sake of the simplicity, however they will have the same reference number with the addition of an apex.

In the second embodiment, the movement device 20' of the valve member 10' is of a mechanical type.

The device 1' comprises a membrane 9' made of an elastically deformable material disposed outside the first wall 30' of the culture chamber 2', more precisely between the first wall 30' and movement device 20'. Preferably, the membrane 9' should be placed between the movement device 20' and pre-chamber 70', if is present. The movement device 20' mechanically interacts with the valve member 10' by said membrane 9'.

More specifically, the movement device 20' comprises a thrusting element 21' preferably arranged in the lower compartment 3'A of the base body 3' and disposed in order to be capable of moving the valve member 10' between the closed position (FIG. 3) and open position (FIG. 4), by thrusting it. The presence of the elastically deformable membrane 9' enables to insulate the supplying conduit 7' and pre-chamber 70' (if is present) from the external environment, without preventing a mechanical interaction between the thrusting element 21' and valve member 10'. The illustrated example shows that the thrusting element 21' interacts with the interaction portion 11' of the valve member 10', more precisely with the disc 13'.

Such mechanical-type movement device 20' is adapted to cell suspension culture devices 1' of any size, both for a laboratory use and in the industrial field.

It is observed that the movement device, in both the embodiments of the invention, does not require to be continuously supplied as in the active type known devices, but only when the valve member is intended to be moved. Another advantage of the device, according to the invention, consists in its simple sturdy structure.

A person skilled in the art in order to meet contingent specific needs, could add many additions, modifications or substitutions of elements with other operatively equivalent ones to the described embodiments of the motorized movement device according to the invention, without falling out of the scope of the attached claims.

The invention claimed is:

1. A device for a cell suspension culture comprising:
   a culture chamber comprising a first wall and a second wall delimiting an inner compartment, said first and second walls having an axisymmetric shape and being connected to each other in order to form an inner continuous surface;
   an inlet opening provided in the first wall and suitable to enable a fluid to enter the culture chamber;
   an outlet opening arranged in the second wall and suitable to enable the fluid to exit the culture chamber;
   a supply conduit connected to the inlet opening and suitable to enable to supply the fluid towards the culture chamber through the inlet opening;
   a valve member arranged inside the culture chamber at the inlet opening, the valve member being positioned between and coaxial with the inlet opening and the outlet opening;
   wherein the valve member is displaceable between an open position and a closed position, wherein the open position is defined as when the valve member is distanced from the inlet opening and enables outflow of the fluid to the inside the culture chamber, wherein the closed position is defined as when the valve member tightly closes the inlet opening, wherein the valve member does not close the outlet opening when the valve member is in the open position such that the fluid is enabled to exit the culture chamber at any time; and a movement device for moving the valve member, suitable to cause the valve member to be displaced between the open position and the closed position, said movement device being disposed outside the culture chamber.

2. The device according to claim 1, further comprising a base body inside which one of the first and second walls is arranged, and a lid suitable to be tightly connected to the base body and in which the other one of the first and second walls of the culture chamber is arranged.

3. The device according to claim 2, wherein the supply conduit is connected to the inlet opening via a pre-chamber arranged in the base body.

4. The device according to claim 3, wherein the valve member has an interaction portion comprising a rod and a disc, the interaction portion extending towards the pre-chamber; and wherein the movement device interacts with the interaction portion to cause the valve member to be displaced between the open position and the closed position.

5. The device according to claim 1, wherein the first wall comprises a bottom zone and a joint zone suitable to connect to each other the bottom zone and the second wall, wherein the joint zone has an arc-of-a-circle cross-section having a concavity facing the inside of the culture chamber.

6. The device according to claim 5, wherein the cross-section of the joint zone of the first wall has a curve radius comprised between five and twenty times the height of the inlet port of the fluid passage.

7. The device according to claim 1, wherein the second wall comprises a central zone and an annular zone with an arc-of-a- circle cross-section having a concavity facing the inside of the culture chamber.

8. The device according to claim 7, wherein the cross-section of the annular zone of the second wall has a curve radius comprised between three and ten times the height of the inlet port for the passage of the fluid, and is less than the curve radius of the joining zone of the first wall.

9. The device according to claim 1, wherein in the open position, the valve member opens an inlet port adjacent to the inlet opening for the passage of the fluid, with a predetermined height with respect to the first wall.

10. The device according to claim 9, wherein the outlet opening has a diameter that is at least one of, equal to the predetermined height of the inlet port, and less than the predetermined height of the inlet port.

11. The device according to claim 9, wherein in the open position, the valve member forms an outlet port adjacent to the outlet opening having a predetermined height substantially equal to the predetermined height of the inlet port.

12. The device according to claim 1, wherein the movement device of the valve member comprises a magnetic element, the valve member being provided with a magnetic counter-element suitable to interact with said magnetic element.

13. The device according to claim 1, comprising a membrane made of an elastically deformable material and arranged outside the first wall of the culture chamber, said membrane being arranged between the first wall and the movement device, and wherein the movement device mechanically interacts with the valve member through said membrane.

* * * * *